United States Patent
Hitt et al.

(10) Patent No.: US 11,205,518 B1
(45) Date of Patent: Dec. 21, 2021

(54) SYSTEM AND METHOD TO PROVIDE INDICATIONS OF A SUBJECT'S FITNESS BASED ON VALUES OF FITNESS METRICS FOR THE SUBJECT

(71) Applicant: GoX Studio, Inc., Phoenix, AZ (US)

(72) Inventors: Joseph Karl Hitt, Scottsdale, AZ (US); Robert Bruce Floersheim, West Chester, PA (US)

(73) Assignee: GoX Studio, Inc., Phoenix, AZ (US)

( * ) Notice: Subject to any disclaimer, the term of this patent is extended or adjusted under 35 U.S.C. 154(b) by 0 days.

(21) Appl. No.: 16/947,791

(22) Filed: Aug. 17, 2020

(51) Int. Cl.
*G16H 50/30* (2018.01)
*A61B 5/00* (2006.01)
*G16H 20/70* (2018.01)
*G16H 20/30* (2018.01)
*G16H 20/60* (2018.01)
*A61B 5/103* (2006.01)

(52) U.S. Cl.
CPC ........... *G16H 50/30* (2018.01); *A61B 5/1034* (2013.01); *A61B 5/681* (2013.01); *A61B 5/7275* (2013.01); *A61B 5/7475* (2013.01); *G16H 20/30* (2018.01); *G16H 20/60* (2018.01); *G16H 20/70* (2018.01)

(58) Field of Classification Search
CPC ........ G16H 50/30; G16H 20/60; G16H 20/70; A61B 5/7275
USPC .................................................. 600/300, 301
See application file for complete search history.

(56) References Cited

U.S. PATENT DOCUMENTS

| 7,027,621 | B1* | 4/2006 | Prokoski | G06K 9/00248 |
| | | | | 180/272 |
| 9,579,060 | B1 | 2/2017 | Lisy | |
| 9,980,112 | B1* | 5/2018 | Newby | H04W 4/029 |
| 10,307,101 | B1 | 6/2019 | Miller | |
| 10,959,056 | B1* | 3/2021 | Alsahlawi | H04W 4/029 |
| 11,055,979 | B1 | 7/2021 | Hitt | |

(Continued)

FOREIGN PATENT DOCUMENTS

WO 2017165037 9/2017

OTHER PUBLICATIONS

Definition of correlate. Merriam-Webster Dictionary, retrieved on May 18, 2021; Retrieved from the Internet: <https://www.merriam-webster.com/dictionary/correlate> (Year: 2021) 1 page.

(Continued)

*Primary Examiner* — John R Downey
(74) *Attorney, Agent, or Firm* — Esplin & Associates, PC (57) ABSTRACT

Systems and methods configured to provide indications of a subject's fitness based on values of a fitness metric for the subject are disclosed. Exemplary implementations may: obtain fitness information related to the subject; present, based on a change in the first value indicating a decline in the real-time state of health, a first notification of the first value via a watch wearable by the subject; present, based on the change in the first value indicating the decline in the real-time state of health, a second notification related to the subject via a second watch wearable by a second subject and/or a client computing platform associated with an administrator; and present, based on a change in the second value indicating a decline in the future state of health, a third notification via the watch, one or more other watches, and/or the client computing platform.

18 Claims, 4 Drawing Sheets

(56) References Cited

U.S. PATENT DOCUMENTS

| | | | |
|---|---|---|---|
| 2007/0158128 A1* | 7/2007 | Gratz | B60R 25/241 180/287 |
| 2007/0167162 A1* | 7/2007 | Kim | H04M 1/6066 455/435.1 |
| 2009/0005652 A1* | 1/2009 | Kurtz | A61B 5/4815 600/300 |
| 2011/0029465 A1 | 2/2011 | Ito | |
| 2011/0047508 A1* | 2/2011 | Metzler | H04L 51/32 715/810 |
| 2012/0001876 A1* | 1/2012 | Chervenka | G09G 5/00 345/204 |
| 2012/0143019 A1 | 6/2012 | Russell | |
| 2012/0249797 A1 | 10/2012 | Haddick | |
| 2014/0222522 A1* | 8/2014 | Chait | G06Q 10/0637 705/7.36 |
| 2015/0242769 A1* | 8/2015 | Kezeu | G06Q 10/06314 705/7.11 |
| 2015/0358043 A1 | 12/2015 | Jeong | |
| 2016/0038083 A1 | 2/2016 | Ding | |
| 2016/0058364 A1 | 3/2016 | Ionescu | |
| 2016/0235374 A1* | 8/2016 | Miller | A61B 5/0537 |
| 2016/0278700 A1 | 9/2016 | Lee | |
| 2016/0292988 A1* | 10/2016 | McCleary | G08B 21/0453 |
| 2017/0046496 A1* | 2/2017 | Johnstone | G06F 19/00 |
| 2017/0303187 A1* | 10/2017 | Crouthamel | H04W 56/0015 |
| 2017/0319130 A1 | 11/2017 | Thomas | |
| 2018/0033279 A1* | 2/2018 | Chong | G06Q 10/0633 |
| 2018/0081912 A1* | 3/2018 | Suleiman | G06N 20/20 |
| 2018/0144427 A1* | 5/2018 | Ebesu | G06Q 10/063114 |
| 2018/0147913 A1 | 5/2018 | Bergin | |
| 2018/0153463 A1 | 6/2018 | Nissila | |
| 2018/0330302 A1* | 11/2018 | Peterson | G10L 25/66 |
| 2019/0008687 A1 | 1/2019 | Ishiura | |
| 2019/0073618 A1* | 3/2019 | Kanukurthy | G06Q 10/0635 |
| 2019/0117170 A1 | 4/2019 | Begtrup | |
| 2019/0134396 A1 | 5/2019 | Toth | |
| 2019/0298261 A1 | 10/2019 | Savchenko | |
| 2019/0311809 A1* | 10/2019 | Young | A61B 5/7275 |
| 2019/0343429 A1* | 11/2019 | Elhawary | A61B 5/1126 |
| 2020/0194124 A1* | 6/2020 | Kramer | G16H 70/20 |
| 2020/0205747 A1 | 7/2020 | Mulligan | |
| 2020/0260973 A1 | 8/2020 | Prstojevich | |
| 2020/0279339 A1* | 9/2020 | Akutagawa | A61B 10/0064 |
| 2020/0302452 A1* | 9/2020 | Platt | H04L 67/42 |

OTHER PUBLICATIONS

Definition of value. Merriam-Webster Dictionary, retrieved on May 18, 2021; Retrieved from the Internet: <https:// www.merriam-webster.com/dictionary/value> (Year: 2021) 1 page.

* cited by examiner

SYSTEM AND METHOD TO PROVIDE INDICATIONS OF A SUBJECT'S FITNESS BASED ON VALUES OF FITNESS METRICS FOR THE SUBJECT

FIELD OF THE DISCLOSURE

The present disclosure relates to systems and methods configured to provide indications of a subject's fitness based on values of a fitness metric for the subject.

BACKGROUND

In various circumstances, it may be crucial and/or beneficial to monitor current fitness of a subject and future fitness of the subject. For example, subjects may include a group of workers, elderly, soldiers, and/or other subjects. Convenient presentation of such current and future fitness to notify essential personnel of any changes that indicate an individual subject is at a health risk may be crucial and/or beneficial.

SUMMARY

One aspect of the present disclosure relates to a system configured to provide indications of a subject's fitness based on values of a fitness metric for the subject. The subject may wear a plurality of sensors on their body by which data is collected about the subject. The data may include information related to the heart of the subject, oxygen consumption of the subject, motion of the subject, location of the subject, and/or other data. Such data may be obtained by the present system and utilized to determine changes in various fitness metrics that may indicate a change, good or bad, in real-time health and future health of the subject. Such changes may be presented in notifications via one or more watches worn by the subject, other subjects, and/or client computing platforms associated with administrators. The notifications may allow the subject, the other subjects, and/or the administrators to stay informed about their peers and take precautionary measures (e.g., drinking water, taking a break, eating) as necessary to maintain healthy functionality and prevent future injuries.

One aspect of the present disclosure relates to a system configured to provide indications of a subject's fitness based on values of a fitness metric for the subject. The system may include one or more hardware processors configured by machine-readable instructions. The machine-readable instructions may include one or more instruction components. The instruction components may include computer program components. The instruction components may include one or more of obtaining component, presentation component, control component, and/or other instruction components.

The obtaining component may be configured to obtain fitness information related to the subject and/or other information. The fitness information may include values to fitness metrics for the subject. A first value to a first fitness metric may indicate current fitness of the subject. A second value to a second fitness metric may indicate predictive fitness of the subject. The current fitness of the subject may correspond to a real-time state of health of the subject to perform actions. The predictive fitness of the subject may correspond to a future state of health of the subject.

The presentation component may be configured to present a first notification of the first value via a watch wearable by the subject. The presentation of the first notification may be based on a change in the first value indicating a decline in the real-time state of health. The presentation component may be configured to present a second notification related to the subject via a second watch wearable by a second subject, a client computing platform associated with an administrator, one or more other watches wearable by other subjects, and/or other client computing platforms. The presentation of the second notification may be based on the change in the first value indicating the decline in the real-time state of health. The presentation component may be configured to present a third notification via the watch, the one or more other watches, and/or the client computing platform. The presentation of the third notification may be based on a change in the second value indicating a decline in the future state of health.

As used herein, the term "obtain" (and derivatives thereof) may include active and/or passive retrieval, determination, derivation, transfer, upload, download, submission, and/or exchange of information, and/or any combination thereof. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
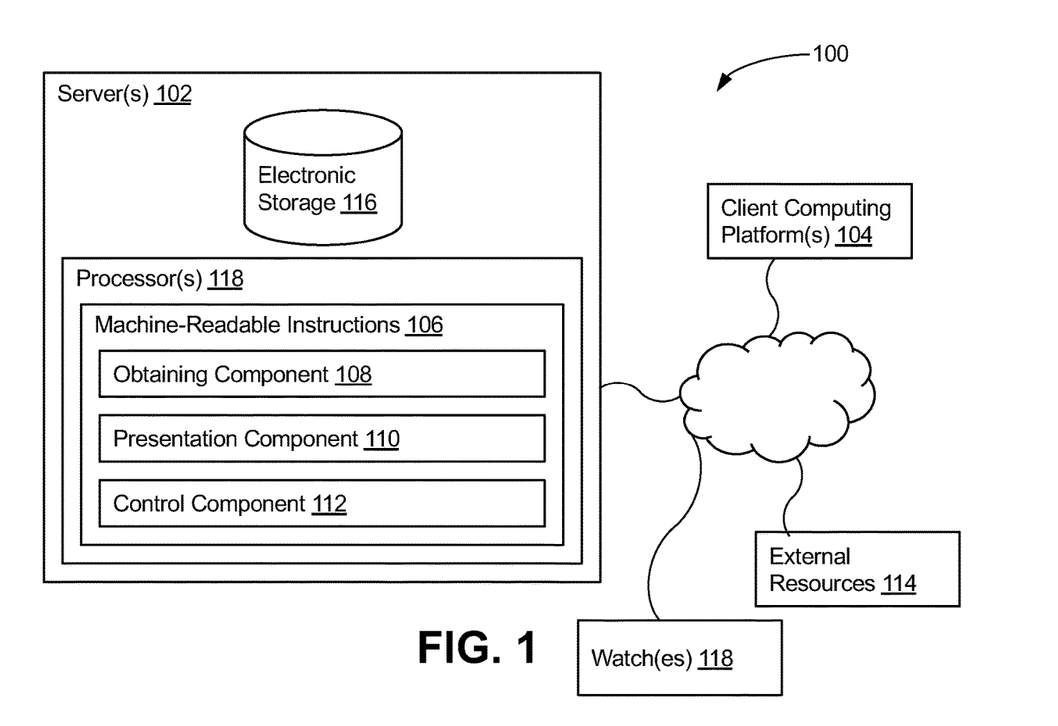
FIG. 1 illustrates a system configured to provide indications of a subject's fitness based on values of a fitness metric for the subject, in accordance with one or more implementations.

FIG. 1 illustrates a system 100 configured to provide indications of a subject's fitness based on values of a fitness metric for the subject, in accordance with one or more implementations. In some implementations, system 100 may include one or more servers 102. Server(s) 102 may be configured to communicate with one or more client computing platforms 104 according to a client/server architecture and/or other architectures. Client computing platform(s)

104 may be configured to communicate with other client computing platforms via server(s) 102 and/or according to a peer-to-peer architecture and/or other architectures. Users may access system 100 via client computing platform(s) 104.

Server(s) 102 may be configured by machine-readable instructions 106. Machine-readable instructions 106 may include one or more instruction components. The instruction components may include computer program components. The instruction components may include one or more of obtaining component 108, presentation component 110, control component 112, and/or other instruction components.

Obtaining component 108 may be configured to obtain fitness information related to the subject and/or other information. The fitness information may include one or more values to one or more fitness metrics for the subject and/or metrics that may affect such fitness metrics. The one or more fitness metrics may include current oxygen consumption metric, maximal oxygen consumption metric, exertion metric, water loss metric, thermal stress and dehydration metric, a heat index metric, a first fitness metric, a second fitness metric, and/or other fitness metrics that are related to or may affect the fitness of the subject. Obtainment of the fitness information (i.e., values to the one or more fitness metrics and/or other metrics) may be in an ongoing manner. The term "ongoing manner" as used herein may refer to continuing to perform an action (e.g., obtain) periodically (e.g., every 30 seconds, every minute, every hour, etc.) until receipt of an indication to terminate. The indication to terminate may include powering off client computing platform 104, powering off a watch 118, charging one or more of a battery of client computing platform 104, charging one or more of a battery of watch 118, resetting client computing platform 104, resetting watch 118, and/or other indications of termination. As used hereinafter, "watch" or variations thereof may refer to watch(es) 118.

In some implementations, one or more sensors may be worn on a body of the subject. The one or more sensors may be configured to generate output signals conveying information related to one or more of location of the subject, motion of the subject, temperature of the subject, cardiovascular parameters of the subject, and/or other information. The one or more sensors may include one or more of an orientation sensor, a location sensor, a pressure sensor, a temperature sensor, a light sensor, an audio sensor, cardiovascular sensor, and/or other sensors.

A location sensor may be configured to generate output signals conveying information related to the location of the subject and/or other information. The information related to the location derived from output signals of a location sensor may define one or more of a geo-location of the subject, an elevation of the subject, and/or other measurements. A location sensor may include one or more of a GPS, an altimeter, and/or other devices. The location of the subject may be a location of a contextual environment of the subject. The contextual environment may be the immediate space surrounding the subject and of which the subject is operating and/or working in. The immediate space may be a particular radius surrounding the subject defined by the location sensor, an operator user, the subject, and/or by other definition. The contextual environment may change over time upon obtainment of an assigned route and/or a predicted route of the subject. The information related to the location may be utilized to obtain ambient condition information from external resources 114 for the location. The ambient condition information may define a temperature, humidity, a current heat index, a future heat index, and/or other ambient condition information.

The information related to the motion of the subject may include acceleration, orientation, speed of motion, joint angles, and/or other information related to the motion of the subject. An orientation sensor may be configured to generate output signals conveying orientation information and/or other information. Orientation information derived from output signals of an orientation sensor may define an orientation of the subject. In some implementations, orientation may refer to one or more of a pitch angle, a roll angle, a yaw angle, heading, pointing direction, and/or other measurements. An orientation sensor may include an inertial measurement unit (IMU) such as one or more of an accelerometer, a gyroscope, a magnetometer, Inclinometers, Electronic nose, Infrared Imagers, Micro-bolometers, micro-displays (DMD), Digital micro-mirror device, Optical Switches, actimetry sensor, and/or other devices.

A pressure sensor may be configured to generate output signals conveying pressure information and/or other information. Pressure information derived from output signals of a pressure sensor may define a force per unit area imparted to the pressure sensor. A pressure sensor may include one or more of a piezoresistive strain gauge, a capacitive pressure sensor, an electromagnetic pressure sensor, a piezoelectric sensor, a strain-gauge, and/or other pressure sensors.

A temperature sensor may be configured to generate output signals conveying information related to the temperature of the subject, the temperature of the contextual environment, and/or other information. The information related to the temperature of the subject derived from output signals of a temperature sensor may define one or more of a temperature at the temperature sensor, temperature within a threshold range of the temperature sensor, biometric information, and/or other measure of temperature of the subject. The biometric information may include one or more of skin temperature readings, internal body temperature readings, and/or other readings. In some implementations, the information related to the temperature of the subject may define one or more of a temperature at the temperature sensor, temperature within a threshold range of the temperature sensor, and/or other measure of temperature of a contextual environment of the subject. A temperature sensor may include one or more of a thermocouple, a resistive temperature Measuring device, an infrared sensor, a bimetallic device, a thermometer, and/or other temperature sensors.

A light sensor may be configured to generate output signals conveying ambient light information and/or other information. The ambient light information derived from output signals of a light sensor may define intensity and/or presence (or absence) of light or other electromagnetic radiation incident on the light sensor. A light sensor may include one or more of a photodiode, an active-pixel sensor, photovoltaic, and/or other sensors.

An audio input sensor may be configured to receive audio input. An audio input sensor may include a sound transducer and/or other sensor configured to convert sound (e.g., air pressure variation) into an electrical signal. By way of non-limiting illustration, an audio input sensor may include a microphone.

One or more cardiovascular sensors may be configured to generate output signals conveying biometric information related to heart, lungs, and circulation of the subject. The biometric information may include values for the cardiovascular parameters of the subject, and/or other values for other biometric parameters. The cardiovascular parameters may include heart rate, a resting heart rate of the subject, a respiratory rate of the subject, blood pressure of the subject, oxygen saturation of the subject, heart rate variability, heartbeat strength, heartbeat rhythm, and/or other cardiovascular parameters. The one or more cardiovascular sensors may include one or more an electrodermal activity (EDA), an electrocardiography (EKG or ECG) sensor, a blood volume pulse (BVP) sensor, a respiration sensor, a blood pressure sensor, and/or other cardiovascular sensors. Other sensors that may convey the biometric information may include one or more of an electromyography (EMG) sensor, and/or other sensors.

The one or more values to the current oxygen consumption metric may indicate a volume of oxygen currently consumed by the subject at the particular moment in time. In some implementations, the values to the current oxygen consumption metric may be obtained, determined, or otherwise derived from the output signals (e.g., from one or more sensors) by obtaining component 108. In some implementations, the one or more values to the current oxygen consumption metric may be stored to electronic storage 116 upon determination. In some implementations, the one or more values to the current oxygen consumption metric may be stored and associated with a corresponding date and/or time.

The one or more values to the maximal oxygen consumption metric may characterize a maximum volume of oxygen the subject has ever consumed. The values to the maximal oxygen consumption metric may be obtained, determined, or otherwise derived from the output signals by obtaining component 108. In some implementations, determining that a particular value to the current oxygen consumption metric is the maximal oxygen consumption may include comparing the particular value with one or more other values of the current oxygen consumption metric stored in electronic storage 116 and defining the values to the maximal oxygen consumption metric based on the comparison(s).

The one or more values to the exertion metric may correlate with exertion of the subject due to work. The exertion of the subject may be the use the energy by the subject due to the work exerted by the subject. The work exerted may be the product of force and displacement of an object. Determining the work exerted by the subject may be based on the information related to the motion of the subject, the values the cardiovascular parameters of the subject, the current oxygen consumption, weight of the object, displacement (e.g., height displacement) of the object, repetition of the motion of the subject, and/or other information. The weight of the object and the displacement of the object may be input prior to exertion of the work by the subject. The values of the exertion metric may be based on a heart rate, the current oxygen consumption value(s), and/or other information. In some implementations, the values of the exertion metric may be determined or otherwise derived by obtaining component 108. The values of the exertion metric may be stored to electronic storage 116. In some implementations, the values of the exertion metric may be stored to electronic storage 116 and associated with a particular date and/or time.

The one or more values to the water loss metric may correlate with estimated percentage of bodyweight of the subject lost in water. The water loss metric may be a system of measurement of how much water (e.g., sweat) the subject has lost. The values of the water loss metric may indicate the estimated percentage, or otherwise estimated amount, of bodyweight loss of the subject. Determining the values of the water loss metric may be determined or otherwise derived by obtaining component 108 and based on the output signals. The values of the water loss metric may be stored to electronic storage 116. In some implementations, the values of the water loss metric may be stored to electronic storage 116 and associated with a particular date and/or time.

The one or more values for the heat index metric may correlate with a current heat index and a future heat index. As used herein, the term "correlate" (and derivatives thereof) may include estimate, quantify, correspond to, combinations thereof, and/or other terms that refer to a relationship in which one value indicates another value. In some implementations, a heat index may be a temperature of a contextual environment of the subject. In some implementations, the heat index may account for air temperature, relative humidity, wind gust, precipitation, an ultraviolet index, visibility, pressure, dew point, wind direction, cloud coverage, and/or other conditions to presume a temperature at which the contextual environment that surrounds the subject feels. As such, the current heat index may represent a current temperature of the contextual environment that surrounds the subject. The future heat index may represent a future temperature the contextual environment may reach on a particular day. The future heat index may represent a future peak temperature of which may be the highest temperature of the particular day. The one or more values for the heat index metric may be obtained, determined, or otherwise derived, by obtaining component 108 based on the information related to the location derived from the output signals of the location sensor and/or external resource 114. The values to the heat index metric may be stored to electronic storage 116. In some implementations, the values to the heat index metric may be stored to electronic storage 116 and associated with a particular date and/or time.

The one or more values to the thermal stress and dehydration metric may indicate a risk related to thermal stress and dehydration that the subject is susceptible to. Dehydration in addition to thermal stress of the body of the subject may include an increase in core body temperature, an increase in heart rate, an increase in oxygen consumption, a decrease in work, a decrease in efficiency of the work, a global cardiopulmonary and neural muscular chain reaction that may decrease cardiac output, stroke volume, cognitive function, and mechanical output, and/or other negative effect. The values of the thermal stress and dehydration metric may be determined by aggregating values of the water loss metric, the heat index information, the exertion metric for the subject, and/or other information. The values of the thermal stress and dehydration metric may be stored to electronic storage 116. In some implementations, the values of the thermal stress and dehydration metric may be stored to electronic storage 116 and associated with a particular date and/or time.

In some implementations, one or more values to a sleep metric may represent sleep of the subject. In some implementations, the one or more values to the sleep metric may be based on the output signals generated by the light sensor, the output signals generated by the actimetry sensor (related to motion of the subject), and/or other output signals. The sleep metric may indicate sleep quality, motion during sleep, hours of sleep, and/or information related to the sleep of the subject. The values of the sleep metric may be stored to electronic storage 116. In some implementations, the values of the sleep metric may be stored to electronic storage 116 and associated with a particular date and/or time.

The one or more values to the first fitness metric may indicate current fitness of the subject. The current fitness of the subject may correspond to a real-time state of health of the subject to perform actions. In some implementations, the real-time state of health of the subject may refer to a general state of health at a given time to function properly based on the values of the various fitness metrics previously described. Functioning properly may include, by way of non-limiting example, the ability to stand, walk, feed oneself, and/or other everyday functions. By way of non-limiting example, actions may include walking, running, lifting, and/or other movement by the subject. The one or more values to the first fitness metric may include a first value and/or other values indicative of the current fitness. The first value may indicate current fitness of the subject at a particular point in time. In some implementations, the current fitness may account for the individual values to the heat index metric, the current oxygen consumption metric, the maximal oxygen consumption metric, the exertion metric, the water loss metric, the thermal stress and dehydration metric, the cardiovascular parameters, the sleep metric, proximity to ill subjects, and/or other fitness metrics at the particular point in time. In some implementations, the first value may be determined or otherwise derived based on the individual values at the particular point in time by obtaining component 108.

The one or more values to the second fitness metric may indicate predictive fitness of the subject. The predictive fitness of the subject may correspond to a future state of health of the subject. The future state of health may refer to a general state of health at a particular point in time in the future to function properly and/or perform the actions. The one or more values to the second fitness metric may include a second value and/or other values indicative of the future fitness. The second value may indicate the fitness of the subject predicted at the particular point in time in the future. The particular point in time in the future may in an hour, in 30 minutes, in 2 hours, in 5 hours, in 72 hours, and/or other length of time in the future. For example, the second value may indicate an influenza-like illness up to 72 hours prior to onset of symptoms. The second value of the second fitness metric may be based on the individual values to the heat index metric, the current oxygen consumption metric, the maximal oxygen consumption metric, the exertion metric, the water loss metric, the thermal stress and dehydration metric, and/or other fitness metrics at a point in time. In such implementations, determining the values of the second fitness metric may include forecast modeling, time series modeling, average risk prediction modeling, weighted average modeling, machine learning, combinations thereof, and/or other determination techniques. In some implementations, the one or more values to the second fitness metric may be obtained, determined or otherwise derived by obtaining component 108.

In some implementations, the individual fitness metrics described herein may be associated with a predictive metric (e.g., the water loss metric and predictive water loss metric). Determining the values to the individual fitness metrics, current or predictive, of the subject may include forecast modeling, time series modeling, average risk prediction modeling, weighted average modeling, machine learning, combinations thereof, and/or other determination techniques. As such, some of the individual values to the heat index metric, the current oxygen consumption metric, the maximal oxygen consumption metric, the exertion metric, the water loss metric, the thermal stress and dehydration metric, and/or other fitness metrics and their individual associated predictive metrics may be indicative of the real-time state of health of the subject (i.e., the first fitness metric) and/or may be indicative of the future state of health of the subject (i.e., the second fitness metric), respectively, or affect such. For example, a third value to the water loss metric may indicate that the loss of water of the subject may be at a moderate risk currently and a fourth value to a predictive water loss metric may indicate that the loss of water of the subject may be at a high risk in the future.

In some implementations, the values to the individual fitness metrics may be part of individual ranges of risk. In some implementations, the range of risk may span between values such as from 0 to 100. The individual ranges of risk may include one or more threshold values. The one or more threshold values may indicate different risks to the state of health, current or predictive, of the subject (e.g., no risk, moderate risk, and dangerous risk). An individual threshold value for a particular fitness metric may be associated with a particular value of the particular fitness metric. For example, the one or more threshold values may include a first threshold. In some implementations, the first threshold may indicate onset of risk to the current state of health. For example, when the current fitness of the subject is at a dangerous risk, the value for the first fitness metric may be at least 40. For example, when the predictive fitness of the subject is at a moderate risk, the value for the second fitness metric may be at least 20.

In some implementations, the individual values to the individual fitness metrics may change. In some instances, the change may indicate a decline or otherwise onset of decline in the real-time state of health and/or the future state of health or an incline (e.g., improvement) in the real-time state of health and/or the future state of health. In some implementations, the changes in the individual values may include meeting or surpassing the one or more thresholds, the value changing (a decrease or increase) by a particular magnitude, the value changing by the particular magnitude within a particular time period (e.g., the first value changing by a magnitude of 20 within one hour), and/or other changes in the individual values to the individual fitness metrics. For example, a change in the first value may include the first value reaching the first threshold.

In some implementations, responsive to the change in the second value indicating the decline in the future state of health, obtaining component 108 may be configured to determine other subjects that are proximate to the subject. Proximity to other individual subjects may be that the other individual subjects are within 4 feet, 6 feet, 7 feet, or other distance from the subject. Determining the other subjects that are proximate may be based on the location of the subject and individual locations of the other subjects that are based on the output signals generated by the location sensors.

In some implementations, obtaining component 108 may be configured to determine a change in values to individual first fitness metrics for individual ones of the other subjects that are proximate. Determining the change in the values to the individual first fitness metrics may be based on the change in the second value. In some implementations, determining the change may be based on the change in the second value, a transmission rate, the current fitness of the other subjects (i.e., first fitness metric value), and/or other information and added to the values to individual first fitness metrics. Determining the change may be different for proximate subjects that are indoors and proximate subjects that are outdoors. In some implementations, the transmission rate may be approximately 1.2 or other value.

For example, current fitness of a second subject proximate to the subject, or value to the first fitness metric, may be 0.1. The second value to the second fitness metric for the subject may be 0.5 and indicate a future illness (e.g., influenza). Upon the subject and the second subject being proximate and indoors, determining the change may include multiplying the second value to the second fitness metric related to the subject (e.g., 0.5) with an absolute value of the transmission rate, 1.2, minus 0.8. A resulting indoor value, 0.2, may be added to the value to the first fitness metric, 0.1, to determine the change in the value to the first fitness metric for the second subject, 0.3.

In some implementations, upon the subject and the second subject being proximate and outdoors, determining the change may include multiplying the second value related to the subject (e.g., 0.5) with 0.1 and with the absolute value of the transmission rate, 1.2, minus 0.8. A resulting outdoor value, 0.02, may be added to the value to the first fitness metric, 0.1, to determine the change in the value to the first fitness metric for the second subject, 0.12. Thus, the current fitness for the proximate second subject may be updated responsive to proximity to the subject. The updated current fitness may indicate a higher risk of the second subject contracting the illness from the subject.

As such, the one or more values to the second fitness metric for the subject may affect one or more values to the individual first fitness metrics for other individual subjects proximate to the subject. In some implementations, the one or more values to the first fitness metric for the subject may affect the one or more values to the individual second fitness metrics for the other subjects. That is, determining that the subject currently is ill based on the first value to the first fitness metric, the risk of the other subjects that are proximate to the subject contracting the illness in the future may be increased significantly or quicker. In some implementations, the change to values to the individual first fitness metrics and/or the individual second fitness metrics may be determined in some other manner.

Presentation component 110 may be configured to present one or more notifications via one or more watches, and/or other client computing platforms. Presentation of the one or more notifications may be based on a change in the values of the individual fitness metrics. In some implementations, a first notification of the first value may be presented via a watch wearable by the subject. Presentation of the first notification may be based on the change in the first value indicating the decline in the real-time state of health. The first notification and other notifications may include one or more of a recommendation, a statement, the values to the fitness metrics, and/or other information. By way of non-limiting example, the recommendation may include role reassignment for the subject, role cancellation, a rest time, a duration for the rest time, mealtimes, a duration for the mealtimes, foods to consume, medication usage, a dosage to the medication, hydration of a liquid (e.g., water), a quantity of the liquid, and/or other recommendations. The role reassignment may include the subject interchanging roles with another subject or appointing the subject to a different role. The role cancellation may include cancelling a shift for a given subject for a particular period of time (e.g., the day, a few days, a week, etc.). That is, a recommendation to go home and/or stay home for the particular period of time may be presented. The particular period of time may be fixed, modifiable by an administrator, determined based on a risk (i.e., values to individual fitness metrics), and/or determined in another manner. The recommendations may be to increase, stabilize, or otherwise facilitate the real-time state of health and/or avoid a decline of the future state of health. The statement may state the fitness metric in which the notification is related, and/or other statements.

In some implementations, presentation component 110 may be configured to present a second notification related to the subject via a second watch wearable by a second subject, one or more other watches wearable by other subjects and/or a client computing platform associated with an administrator. Presentation of the second notification may be based on the change in the first value indicating the decline in the real-time state of health. In some implementations, the one or more other watches may include the second watch. By way of non-limiting example, the administrator may be a supervisor, a caregiver, a nurse, a doctor, and/or other administrator of the subject. The second notification may include one or more of a name of the subject, a role of the subject, a location of the subject, the recommendation, the statement, the first value, the role reassignment so that other subjects may assume the role of the subject, and/or other notifications. The statement may state the name of the subject, the fitness metric in which the notification is related, and/or other statements. By way of non-limiting example, the statement may state "Jane is over exerted" or "Jane's heartrate is currently too high" among others. As such, the administrator and/or the other subjects may be aware of information related to the subject.

In some implementations, presentation component 110 may be configured to present a third notification via the watch, one or more other watches, the client computing platforms, and/or other devices. Presentation of the third notification may be based on a change in the second value indicating the decline in the future state of health. The one or more other watches may be associated and worn by other subjects. The third notification may include one or more of the name of the subject, an identifier of the subject, the role of the subject, the location of the subject, the recommendation (the same as or similar to the recommendation presented in the first notification), the statement (the same as or similar to the statement presented in the first notification), the second value, the change in the values to the individual first fitness metrics, changes in the values to the individual second fitness metrics, and/or other notifications. In some implementations, the statement presented via the watches may include a warning. The warning may state that an ill subject is proximate based on the location the subject and the location of individual other subjects wearing the one or more other watches. In some implementations, the warning may be presented to the other subjects that are proximate (e.g., within a particular distance value such as 6 feet) to the ill subject. The identifier of the subject may uniquely identify the subject from other subjects or other administrators within system 100 and/or other system.

In some implementations, the presentation of the first notification, the second notification, the third notification, and/or other notifications may include one or more of a color scheme, symbols, graphics, and/or other visuals. In some implementations, the color scheme may include colors that are individually associated with the different fitness risks (e.g., no risk, moderate risk, dangerous risk) or risks related to one or more of the fitness metrics. For example, the colors in the color scheme may include green for no risk, amber for moderate risk, and red for dangerous risk for the current fitness, predictive fitness, and/or other fitness metrics corresponding to the subject. In some implementations, the notifications may include a map. The map may provide a visualization of the locations of the individual subjects to indicate proximities of the subjects to each other and risks to current and/or predictive fitness associated with those proximities. The visualization may include symbols that include the color scheme. That is, a symbol representing a predictively ill subject (e.g., influenza) may be red. A symbol representing a subject that is 5 feet in proximity to the predictively ill subject may be yellow indicating a moderate risk to their current and/or predictive fitness based on their proximity.

In some implementations, control component 112 may be configured to immediately restrict operation of particular machinery, access through particular doors by the subject, shifts/roles, and/or other operations. The immediate restriction may be based on the change in one or more of the values to the individual fitness metrics. By way of non-limiting example, machinery may include motor vehicles (e.g., cars, semi-trucks, golf carts, etc.), water vehicles (e.g., fishing boats, jet skis, ships, etc.), aircrafts (e.g., jets, commercial planes, helicopters, etc.), electric vehicles (e.g., golf carts, wheelchairs, etc.), power tools (e.g., lawn mower, chainsaws, nail gun, etc.), industrial machinery (e.g., for article or product manufacturing), and/or other machinery. In some implementations, access through one or more doors by the subject may be restricted. Restriction of access through doors may facilitate preventing the subject from entering environments or zones of which may exacerbate the values of individual fitness metrics (e.g., the current fitness). In some implementations, a shift or the role of the subject may be restricted or cancelled to prevent the subject from contact with and/or exposure to other subjects (e.g., upon prediction of an illness). By way of non-limiting example, operation of particular machinery (e.g., a forklift) may be immediately restricted based on the change in the first value (i.e., the current fitness). For example, a particular door may lead to a room with low humidity and the subject may be restricted from entering upon an indication of a decline in the current fitness of the subject and/or an indication of a high percentage of bodyweight of the subject lost in water.

In some implementations, control component 112 may be configured to restrict operations of particular machinery and/or access through particular doors by the subject at a particular time. The particular time of the restrictions may be based on the change in the second value. In other words, the change in the second value may indicate that the predictive fitness of the subject may decline at a particular time such as in 1.5 hours. Thus, machinery and/or door access may restriction for the subject in 1.5 hours. In some implementations, such restrictions may change or be eliminated upon further changes in the second value, the first value (indicating the current fitness), and/or other values of the individual fitness metrics responsive to the subject taking precautionary measures (e.g., from recommendations presented) such as taking a rest time or drinking water.

In some implementations, control component 112 may be configured to receive input to allow the operation of particular machinery and/or access through particular doors by the subject. The input may be from an administrator and/or the one or more other subjects. Control component 112 may be configured to override one or more of the restrictions imposed based on the input. In some implementations, for control component 112 to override one or more restrictions, input may be required from a particular number of other subjects. For example, one other subject may not enter input to override the restrictions for a given subject, but at least 4 other subjects must enter input to override the restrictions. This may facilitate safety of the given subject and eliminate inappropriate use of overriding restrictions. In some implementations, for control component 112 to override one or more restrictions, the input may be required from a particular administrator. For example, the particular administrator may be an on-sight nurse, doctor, supervisor, and/or other administrator.

In some implementations, control component 112 may be configured to activate additional resources and/or remove the subject from the role. The activation and/or removal may be based on the change in the first value, the second value, and/or other values to other individual fitness metrics. The additional resources may include on-call subjects so that the on-call subjects are assigned at least the role of the subject, a temporary automated resources (e.g., auto pilot), an order or purchase of equipment, and/or other additional resources that may alleviate the decline in the current and/or predictive fitness of a given subject. In some implementations, the statement presented to the other subjects via one or more watches and/or presented via client computing platforms may state the activation and/or the removal of the subject. For example, the presentation of the third notification (with the statement) to the one or more other subjects via their associated watches may state that the subject is being removed from their role and they are replacing the subject. The presentation of the third notification (with the statement) to the administrator via the client computing platform may state such removal of the subject from their role and replacement of the subject with the one or more other subjects.

Figure 3:
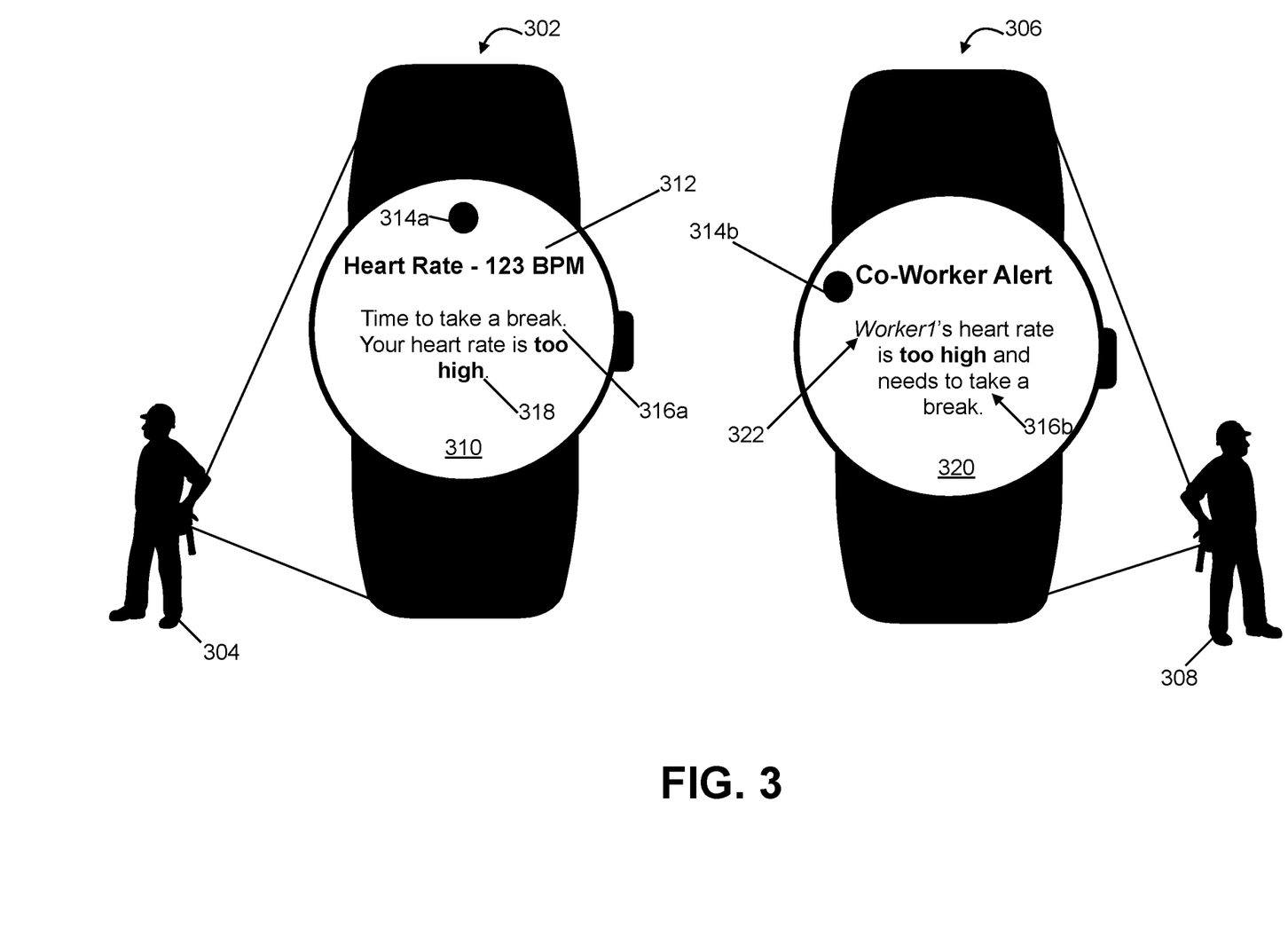
FIG. 3 illustrates an example implementation of a system configured to provide indications of a subject's fitness based on values of a fitness metric for the subject, in accordance with one or more implementations.

FIG. 3 illustrates an example implementation of a system configured to provide indications of a subject's fitness based on values of a fitness metric for the subject, in accordance with one or more implementations. FIG. 3 may illustrate a watch 302 wearable by a subject 304 and a watch 306 wearable by a subject 308. Watch 302 may present a notification 310. Notification 310 may include value 312 to a fitness metric (e.g., heart rate), a color scheme 314a, and a recommendation 316a, and a statement 318. The value 312 may be the current value to the fitness metric of which changed and statement 318 may state a risk related to the change. As such, value 312 and statement 318 may indicate a decline in and/or risk to the current fitness of subject 304. Color scheme 314a (e.g., red) may visually indicate the risk (e.g., high risk). Recommendation 316a may recommend for subject 304 to take a break to improve value 312 and the risk.

Watch 306 may present a notification 320. Notification 320 may include a statement 322, a recommendation 316b, and a color scheme 314b. Statement 322 may include a name of subject 304 (e.g., Worker1) currently at risk and a current risk related to the fitness metric (e.g., "heart rate is too high") of subject 304. Statement 322 may be similar to statement 318. Recommendation 316b may be the same as or similar recommendation as 316a and may refer to subject 304. Color scheme 314b may be similar to or the same as color scheme 314a such that the risk of subject 304 may be visually presented to subject 308.

Figure 4:
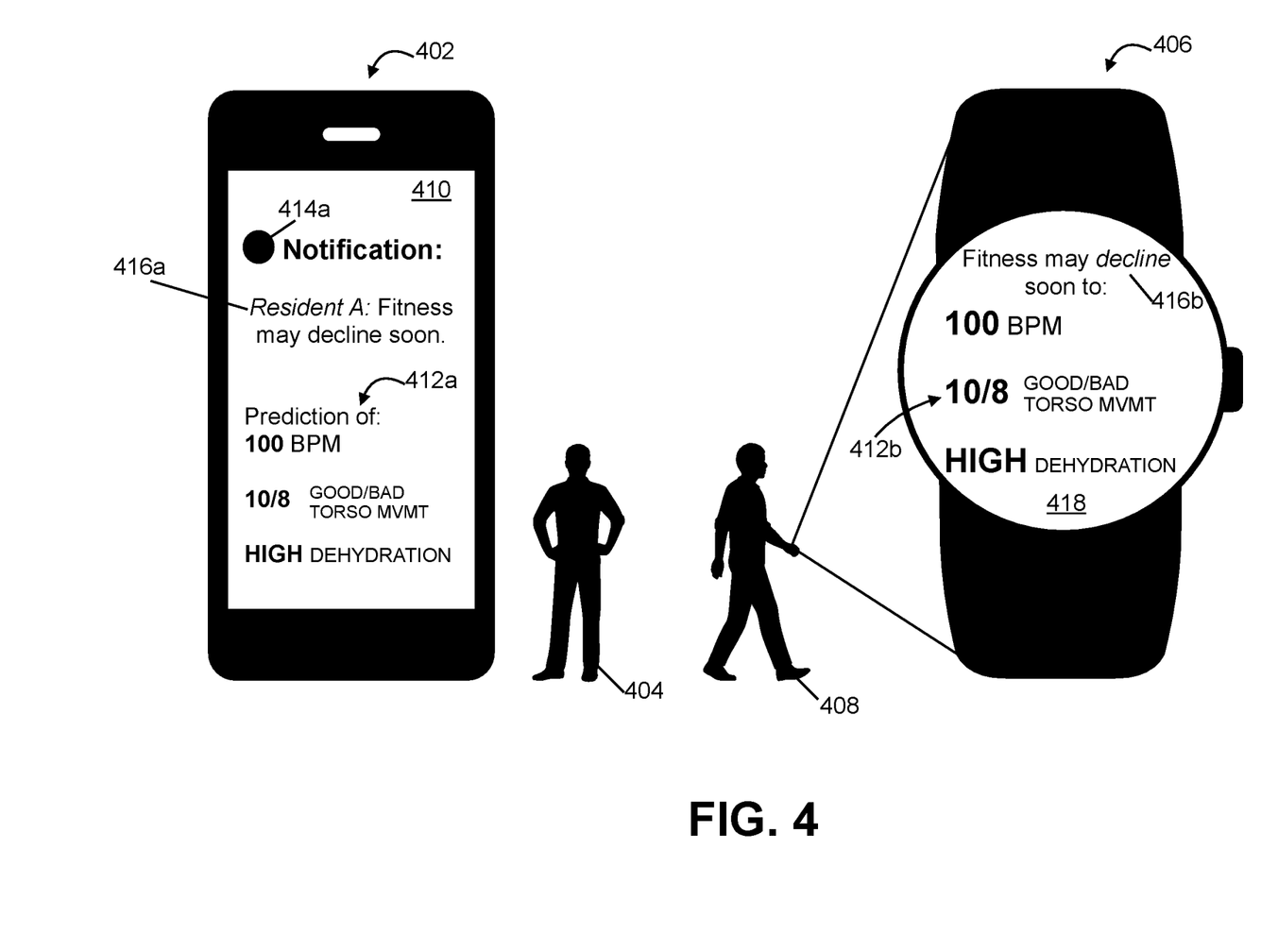
FIG. 4 illustrates an example implementation of a system configured to provide indications of a subject's fitness based on values of a fitness metric for the subject, in accordance with one or more implementations.

FIG. 4 illustrates an example implementation of a system configured to provide indications of a subject's fitness based on values of a fitness metric for the subject, in accordance with one or more implementations. FIG. 4 may illustrate a smartphone 402 associated with an administrator 404 and a watch 406 wearable by a subject 408. Smartphone 402 may display notification 410 to administrator 404. Notification 410 may include values 412a to fitness metrics (e.g., BPM, Torso Movement, Dehydration), a color scheme 414a, and a statement 416a. Statement 416a may include a name of a resident (e.g., Resident A) that refers to a subject wearing a watch (e.g., watch 406 worn by subject 408). Statement 416a may state that fitness of subject 408 may decline soon.

Statement 416*a* may refer to more than one value such as values to BPM, Torso Movement, and Dehydration. Values 412*a* may be predictive values to the fitness metrics related to subject 408.

Watch 406 may display a notification 418. Notification 418 may include values 412*b* to the fitness metrics and a statement 416*b*. Statement 416*b* may state a prediction that the fitness of subject 408 may decline soon to values 412*b*. Values 412*b* may be predictive values to the fitness metrics and may be the same as or similar to values 412*a*. Values 412*b* may be displayed in a color (e.g., amber) to visually indicate a risk (e.g., moderate risk) of predictive fitness of subject 408.

Referring back to FIG. 1, in some implementations, server(s) 102, client computing platform(s) 104, and/or external resources 114 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 114 may be operatively linked via some other communication media.

A given client computing platform 104 may include one or more processors configured to execute computer program components. The computer program components may be configured to enable an expert or user associated with the given client computing platform 104 to interface with system 100 and/or external resources 114, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 114 may include sources of information outside of system 100, external entities participating with system 100, and/or other resources. In some implementations, some or all of the functionality attributed herein to external resources 114 may be provided by resources included in system 100.

Server(s) 102 may include electronic storage 116, one or more processors 118, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 116 may comprise non-transitory storage media that electronically stores information. The electronic storage media of electronic storage 116 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 116 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 116 may include one or more virtual storage resources (e.g., cloud storage, a virtual private network, and/or other virtual storage resources). Electronic storage 116 may store software algorithms, information determined by processor(s) 118, information received from server(s) 102, information received from client computing platform(s) 104, and/or other information that enables server(s) 102 to function as described herein.

Processor(s) 118 may be configured to provide information processing capabilities in server(s) 102. As such, processor(s) 118 may include one or more of a digital processor, an analog processor, a digital circuit designed to process information, an analog circuit designed to process information, a state machine, and/or other mechanisms for electronically processing information. Although processor(s) 118 is shown in FIG. 1 as a single entity, this is for illustrative purposes only. In some implementations, processor(s) 118 may include a plurality of processing units. These processing units may be physically located within the same device, or processor(s) 118 may represent processing functionality of a plurality of devices operating in coordination. Processor(s) 118 may be configured to execute components 108, 110, and/or 112, and/or other components. Processor(s) 118 may be configured to execute components 108, 110, and/or 112, and/or other components by software; hardware; firmware; some combination of software, hardware, and/or firmware; and/or other mechanisms for configuring processing capabilities on processor(s) 118. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, and/or 112 are illustrated in FIG. 1 as being implemented within a single processing unit, in implementations in which processor(s) 118 includes multiple processing units, one or more of components 108, 110, and/or 112 may be implemented remotely from the other components. The description of the functionality provided by the different components 108, 110, and/or 112 described below is for illustrative purposes, and is not intended to be limiting, as any of components 108, 110, and/or 112 may provide more or less functionality than is described. For example, one or more of components 108, 110, and/or 112 may be eliminated, and some or all of its functionality may be provided by other ones of components 108, 110, and/or 112. As another example, processor(s) 118 may be configured to execute one or more additional components that may perform some or all of the functionality attributed below to one of components 108, 110, and/or 112.

Figure 2:
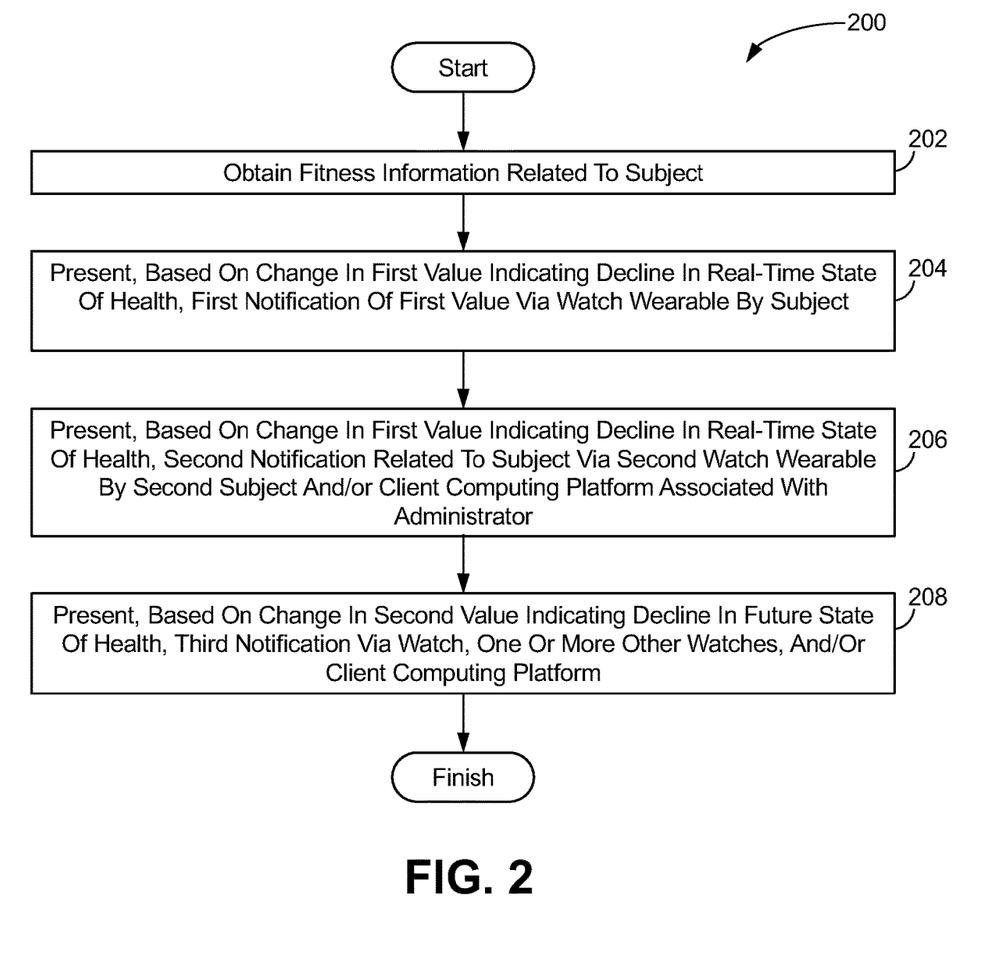
FIG. 2 illustrates a method to provide indications of a subject's fitness based on values of a fitness metric for the subject, in accordance with one or more implementations.

FIG. 2 illustrates a method 200 configured to provide indications of a subject's fitness based on values of a fitness metric for the subject, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include obtaining fitness information related to the subject. The fitness information may include values to fitness metrics for the subject. Operation 202 may be performed by one or more hardware processors configured by machine-readable instructions including a component that is the same as or similar to obtaining component 108, in accordance with one or more implementations.

An operation 204 may include presenting, based on a change in the first value indicating a decline in the real-time state of health, a first notification of the first value via a watch wearable by the subject. Operation 204 may be performed by one or more hardware processors configured by machine-readable instructions including a component that is the same as or similar to presentation component 110, in accordance with one or more implementations.

An operation 206 may include presenting, based on the change in the first value indicating the decline in the real-time state of health, a second notification related to the subject via a second watch wearable by a second subject and/or a client computing platform associated with an administrator. Operation 206 may be performed by one or more hardware processors configured by machine-readable instructions including a component that is the same as or similar to presentation component 110, in accordance with one or more implementations.

An operation 208 may include presenting, based on a change in the second value indicating a decline in the future state of health, a third notification via the watch, the one or more other watches, and/or the client computing platform. Operation 208 may be performed by one or more hardware processors configured by machine-readable instructions including a component that is the same as or similar to presentation component 110, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to provide indications of a subject's fitness based on values of fitness metrics for the subject, the system comprising:
one or more processors configured by machine-readable instructions to:
obtain, in an ongoing manner based on sensors, fitness information related to subjects, wherein the fitness information includes values to fitness metrics for the subjects, wherein a first value to a first fitness metric indicates current fitness of a first subject, and a second value to a second fitness metric indicates predictive fitness of the first subject, wherein the current fitness of the subjects corresponds to a real-time state of health of the subjects to perform actions, wherein the predictive fitness of the subjects corresponds to a future state of health of the subjects;
determine a change in the first value indicating a decline in the real-time state of health based on the ongoing obtainment of the fitness information including values to the second fitness metric that indicates the predictive fitness for other subjects proximate to the subject and the first value, a transmission rate, and a constant, wherein a third value is calculated based on individual ones of the values to the second fitness metric for the other subjects, the transmission rate, and the constant and is added to the first value;
present, based on the change in the first value indicating the decline in the real-time state of health, a first notification of the first value via a watch wearable by the subject;
present, based on the change in the first value indicating the decline in the real-time state of health, a second notification related to the subject via a second watch wearable by a second subject and/or a client computing platform associated with an administrator, wherein the first notification includes a role reassignment and a statement related to the first value for the subject, and wherein the second notification includes a name of the subject, a location of the subject, and the role reassignment;
determine a change in the second value indicating a decline in the future state of health based on the ongoing obtainment of the fitness information;
present, based on the change in the second value indicating the decline in the future state of health, a third notification via the watch, one or more other watches wearable by other subjects, and the client computing platform, wherein the third notification includes the second value, a second statement related to the second value, and secondary recommendation of a second role reassignment related to the subject and the other subjects; and
immediately restrict, based on the change in the first value, operation of particular machinery and/or access through particular doors by the subject.

2. The system of claim 1, wherein the first notification includes a recommendation.

3. The system of claim 2, wherein the recommendation includes the role reassignment for the subject, a rest time and duration, mealtimes, role cancellation, hydration of a liquid, and/or a quantity of the liquid.

4. The system of claim 1, wherein:
the second notification includes a role of the subject, the statement and/or the first value so that the second subject assumes the role of the subject, and
the third notification includes the name of the subject, an identifier of the subject, the role of the subject, and the location of the subject.

5. The system of claim 4, wherein the one or more processors are further configured by machine-readable instructions to:
activate, based on the change in the second value, additional resources and remove the subject from the role, wherein the statement states the activation and the removal.

6. The system of claim 1, wherein the presentation of the first notification, the second notification, and/or the third notification may include a color scheme, wherein the color scheme includes colors that are individually associated with the different fitness risks.

7. The system of claim 1, wherein the one or more processors are further configured by machine-readable instructions to:
restrict, based on the change in the second value, operation of particular machinery and/or access through particular doors by the subject at a particular time based on the change in the second value.

8. The system of claim 1, wherein the one or more processors are further configured by machine-readable instructions to:
receive input from an administrator and/or the one or more other subjects to allow the operation of particular machinery and/or access through particular doors by the subject; and
override the restriction based on the input.

9. The system of claim 1, wherein the one or more processors are further configured by machine-readable instructions to:
determine, responsive to the change in the second value indicating the decline in the future state of health, other subjects that are proximate to the subject;
determine, based on the change in the second value, a change in values to individual first fitness metrics for individual ones of the other subjects; and
present, via the one or more other watches, the third notification to the other subjects that are proximate, wherein the third notification includes a recommendation, a statement, and/or the change in the values to the individual first fitness metrics.

10. A method to provide indications of a subject's fitness based on values of fitness metrics for the subject, the method comprising:
obtaining, in an ongoing manner based on sensors, fitness information related to subjects, wherein the fitness information includes values to fitness metrics for the subjects, wherein a first value to a first fitness metric indicates current fitness of a first subject, and a second value to a second fitness metric indicates predictive fitness of the first subject, wherein the current fitness of the subjects corresponds to a real-time state of health of the subjects to perform actions, wherein the predictive fitness of the subjects corresponds to a future state of health of the subjects;
determining a change in the first value indicating a decline in the real-time state of health based on the ongoing obtainment of the fitness information including values to the second fitness metric that indicates the predictive fitness for other subjects proximate to the subject and the first value, a transmission rate, and a constant, wherein a third value is calculated based on individual ones of the values to the second fitness metric for the other subjects, the transmission rate, and the constant and is added to the first value;
presenting, based on the change in the first value indicating the decline in the real-time state of health, a first notification of the first value via a watch wearable by the subject;
presenting, based on the change in the first value indicating the decline in the real-time state of health, a second notification related to the subject via a second watch wearable by a second subject and/or a client computing platform associated with an administrator, wherein the first notification includes a role reassignment and a statement related to the first value for the subject, and wherein the second notification includes a name of the subject, a location of the subject, and the role reassignment;
determining a change in the second value indicating a decline in the future state of health based on the ongoing obtainment of the fitness information;
presenting, based on the change in the second value indicating the decline in the future state of health, a third notification via the watch, one or more other watches wearable by other subjects, and the client computing platform, wherein the third notification includes the second value, a second statement related to the second value, and secondary recommendation of a second role reassignment related to the subject and the other subjects; and
immediately restricting, based on the change in the first value operation of particular machinery and/or access through particular doors by the subject.

11. The method of claim 10, wherein the first notification includes a recommendation.

12. The method of claim 11, wherein the recommendation includes the role reassignment for the subject, a rest time and duration, mealtimes, role cancellation, hydration of a liquid, and/or a quantity of the liquid.

13. The method of claim 10, wherein:
the second notification includes a role of the subject, the statement and/or the first value so that the second subject assumes the role of the subject, and
the third notification includes the name of the subject, an identifier of the subject, the role of the subject, and the location of the subject.

14. The method of claim 13, further comprising:
activating, based on the change in the second value, additional resources and remove the subject from the role, wherein the statement states the activation and the removal.

15. The method of claim 10, wherein the presentation of the first notification, the second notification, and/or the third notification may include a color scheme, wherein the color scheme includes colors that are individually associated with the different fitness risks.

16. The method of claim 10, further comprising:
restricting, based on the change in the second value, operation of particular machinery and/or access through particular doors by the subject at a particular time based on the change in the second value.

17. The method of claim 10, further comprising:
receiving input from an administrator and/or the one or more other subjects to allow the operation of particular machinery and/or access through particular doors by the subject; and
overriding the restriction based on the input.

18. The method of claim 10, further including:
determining, responsive to the change in the second value indicating the decline in the future state of health, other subjects that are proximate to the subject;
determining, based on the change in the second value, a change in values to individual first fitness metrics for individual ones of the other subjects; and
presenting, via the one or more other watches, the third notification to the other subjects that are proximate, wherein the third notification includes a recommendation, a statement, and/or the change in the values to the individual first fitness metrics.

* * * * *